__United States Patent__ [19]

Fujioka et al.

[11] Patent Number: 4,491,537

[45] Date of Patent: Jan. 1, 1985

[54] TERTIARY HYDROXYL CARBOXALDEHYDES AND ORGANOLEPTIC USE THEREOF

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[21] Appl. No.: 511,965

[22] Filed: Jul. 8, 1983

[51] Int. Cl.$^3$ .............................................. A61K 7/46
[52] U.S. Cl. ................................. 252/522 R; 568/442; 424/69; 424/70; 252/174.11; 252/8.6
[58] Field of Search .................. 568/442; 252/522 R, 252/522 A

[56] References Cited

U.S. PATENT DOCUMENTS

| | | | |
|---|---|---|---|
| 3,632,396 | 1/1972 | Perre-Zamora | 117/76 P |
| 3,948,818 | 4/1976 | Tomiyama et al. | 252/542 |
| 4,113,781 | 9/1978 | Aquila et al. | 568/442 |
| 4,435,585 | 3/1984 | Crameri et al. | 568/442 |

FOREIGN PATENT DOCUMENTS 1007948 5/1977 Canada .

*Primary Examiner*—Anton H. Sutto
*Attorney, Agent, or Firm*—Arthur L. Liberman

[57] ABSTRACT

Described are tertiary hydroxyl carboxaldehydes defined according to the generic structure:

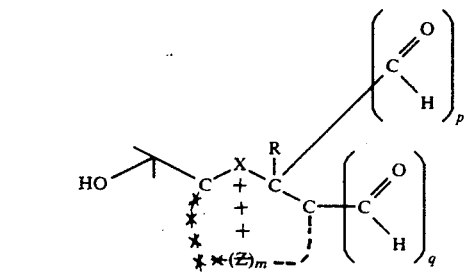

wherein the lines

· · · · · and

— — — — — and/or

+ + + + + represent covalent carbon-carbon bonds when m does not=0; and wherein the lines

+ + + + +

· · · · · and

— — — — — do not represent any bonds when m=0; wherein R represents hydrogen or methyl; wherein p and q each represents 0 or 1 with the proviso that p=1 when q=0 and p=0 when q=1; wherein X and Z each represent (Abstract continued on next page.)

GLC PROFILE FOR FRACTION 6 OF EXAMPLE I.

FIG. 2 NMR SPECTRUM FOR EXAMPLE I, PEAK "II" OF FIG. I

GLC PROFILE FOR EXAMPLE II.
CRUDE

GLC PROFILE FOR EXAMPLE II,
FRACTION I.
REDISTILLATION

NMR SPECTRUM FOR EXAMPLE II.

IR SPECTRUM FOR EXAMPLE II.

GLC PROFILE FOR BULKED FRACTIONS 5 AND 6, OF EXAMPLE III.

1st DISTILLATION

GLC PROFILE FOR FRACTION 6 OF EXAMPLE IV.
2nd DISTILLATION

NMR SPECTRUM FOR FRACTION 6 OF EXAMPLE III, FIRST DISTILLATION

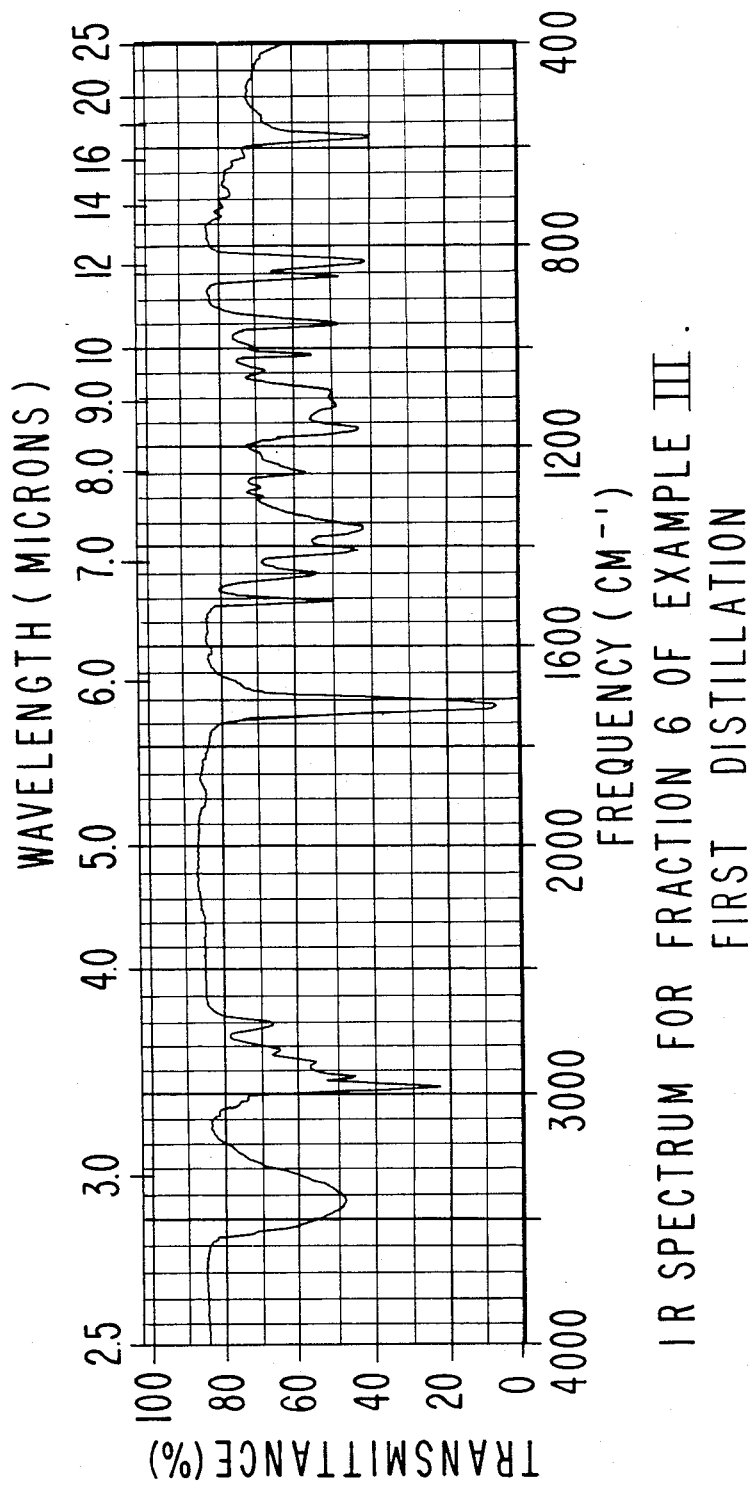

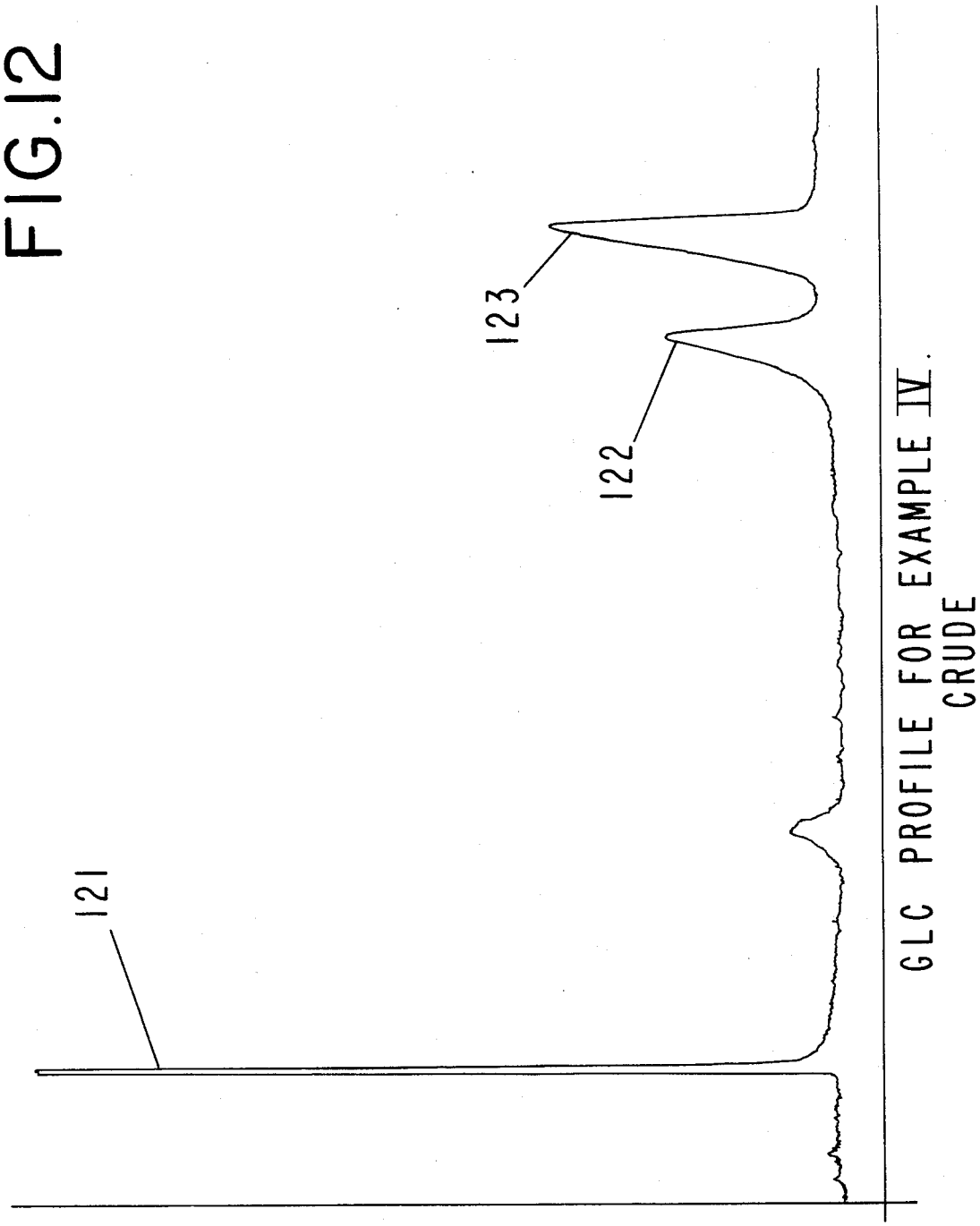

NMR SPECTRUM FOR FRACTION 4 OF EXAMPLE IV. 2nd DISTILLATION

TERTIARY HYDROXYL CARBOXALDEHYDES AND ORGANOLEPTIC USE THEREOF

BACKGROUND OF THE INVENTION

This invention relates to tertiary hydroxyl carboxaldehydes defined according to the structure:

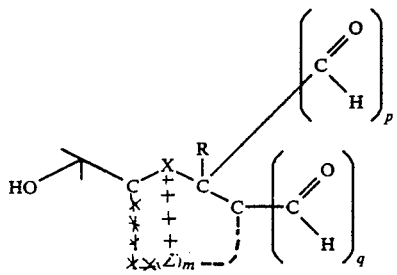

wherein the lines

✕ ✕ ✕ ✕ ✕ and

— — — — — and/or

+ + + + + represent covalent carbon-carbon bonds when m does not=0; and wherein the lines

+ + + + +

✕ ✕ ✕ ✕ ✕ and

— — — — — do not represent any bonds when m=0; wherein R represents hydrogen or methyl; wherein p and q each represents 0 or 1 with the proviso that p=1 when q=0 and p=0 when q=1; wherein X and Z each represent one or more carbon atoms required to complete a bicyclo ring with the lines

+ + + + +

✕ ✕ ✕ ✕ ✕ and

— — — — — representing carbon-carbon bonds; wherein X and Z complete a phenyl moiety when the line

— — — — — represents no bond; wherein X and Z complete a cycloalkyl ring moiety with the lines

✕ ✕ ✕ ✕ ✕ and

+ + + + + represent carbon-carbon bonds and with the line

— — — — — representing no bond; and wherein when m is 0, X represents an alkylene moiety, produced according to an oxo reaction on a member of the unsaturated genus having the structure:

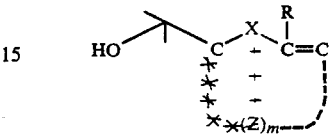

and organoleptic uses thereof particularly augmenting or enhancing the aroma of perfume compositions, colognes and perfumed articles.

Inexpensive chemical compounds which can provide woody, nutty, floral, lilac, green, peach-like, balsamic and fresh air dried linen aromas with minty, floral, cinnamon-like and green topnotes are highly desirable in the art of perfumery. Many of the natural materials which provide such fragrances and contribute such desired nuances to perfumery compositions and perfumed articles are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree, or they contribute undesirable or unwanted odor to the compositions.

U.S. Pat. No. 4,357,247 issued on Nov. 2, 1982 discloses aliphatic $C_{11}$ branched chain aldehydes and alcohols, defined according to the generic structure:

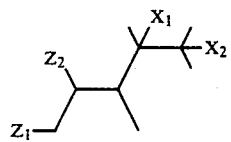

wherein one of $X_1$ or $X_2$ is hydrogen and the other of $X_1$ or $X_2$ is methyl; and wherein one of $Z_1$ or $Z_2$ is hydrogen and the other of $Z_1$ or $Z_2$ is hydroxymethyl having the structure:

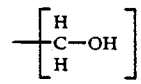

or carboxaldehyde having the structure:

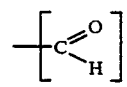

for use in augmenting or enhancing the aroma of perfume compositions, colognes and perfumed articles. The resulting compounds and compositions of matter provide citrusy, green, melony, woody, peanut oil-like and vetiver-like aroma nuances. The compounds of U.S. Pat. No. 4,357,247 are different in kind insofar as their structure and organoleptic properties are concerned from the compounds of the instant application.

Furthermore, $C_{11}$ aliphatic alcohols and aldehydes are well known in the art of perfumery, e.g., n-undecanal and n-undecanol. Oxo reaction products on hydrocarbon compounds are also well known in the perfumery industry aside from U.S. Pat. No. 4,357,247. Thus, U.S. Pat. No. 4,146,505 discloses the formation of hydroxymethyl-formyl-tricyclo[5,2,1,0$^{2,6}$]decane having the structure:

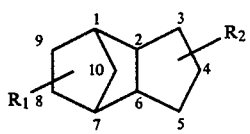

wherein $R_1$ and $R_2$ are the hydroxymethyl group, $CH_2OH$ or the formyl group CHO and $R_1$ represents $CH_2OH$ when $R_2$ is CHO and vice versa. This polycyclic carboxaldehyde alcohol is indicated to be useful as a musk aroma imparting or augmenting material. The material is indicated to be produced by reaction of carbon monoxide and hydrogen with dicyclopentadiene. Other oxo reaction products on unsaturated hydrocarbons are known in the perfumery industry, for example, "Vandor-B", which is the oxo reaction product of carbon monoxide and hydrogen on diiosbutylene. This material has been produced by International Flavors & Fragrances Inc., the assignee of the instant patent application, for several years.

Nothing in the prior art however, discloses the compounds defined according to the structure:

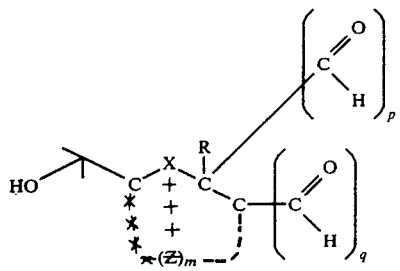

produced by oxo reaction on compounds defined according to the structure:

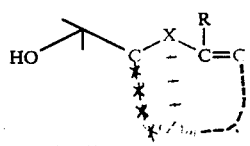

wherein the lines

\*\*\*\*\* and

― ― ― ― ― and/or

+ + + + + represent covalent carbon-carbon bonds when m does not=0; and wherein the lines

+ + + + +

\*\*\*\*\* and

― ― ― ― ― do not represent any bonds when m=0; wherein R represents hydrogen or methyl; wherein p and q each represents 0 and 1 with the proviso that p=1 when q=0 and p=0 when q=1; wherein X and Z each represent one or more carbon atoms required to complete a bicyclo ring with the lines

+ + + + +

\*\*\*\*\* and

― ― ― ― ― representing carbon-carbon bonds; wherein X and Z complete a phenyl moiety when the line

― ― ― ― ― represents no bond; wherein X and Z complete a cycloalkyl ring moiety with the lines

\*\*\*\*\* and

+ + + + + represent carbon-carbon bonds and with the line

― ― ― ― ― representing no bond; and wherein when m is 0, X represents an alkylene moiety.

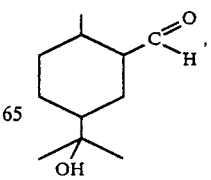

-continued

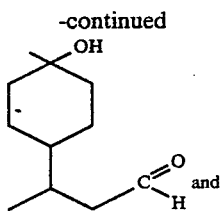
and

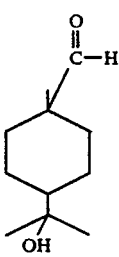

Figure 1:
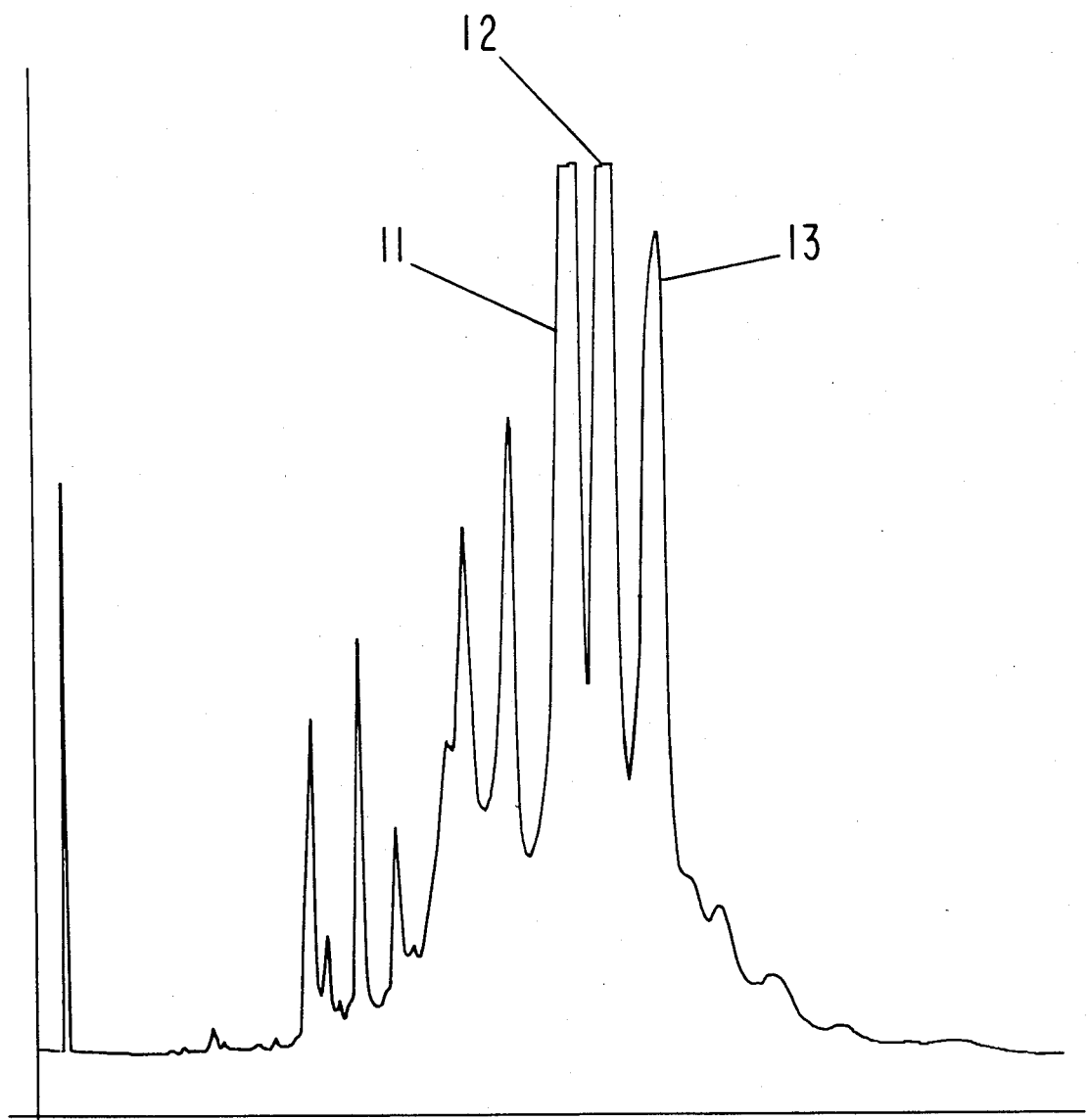
FIG. 1 is the GLC profile for fraction 6 of the distillation product of the reaction product containing the compounds having the structures.
Figure 2:
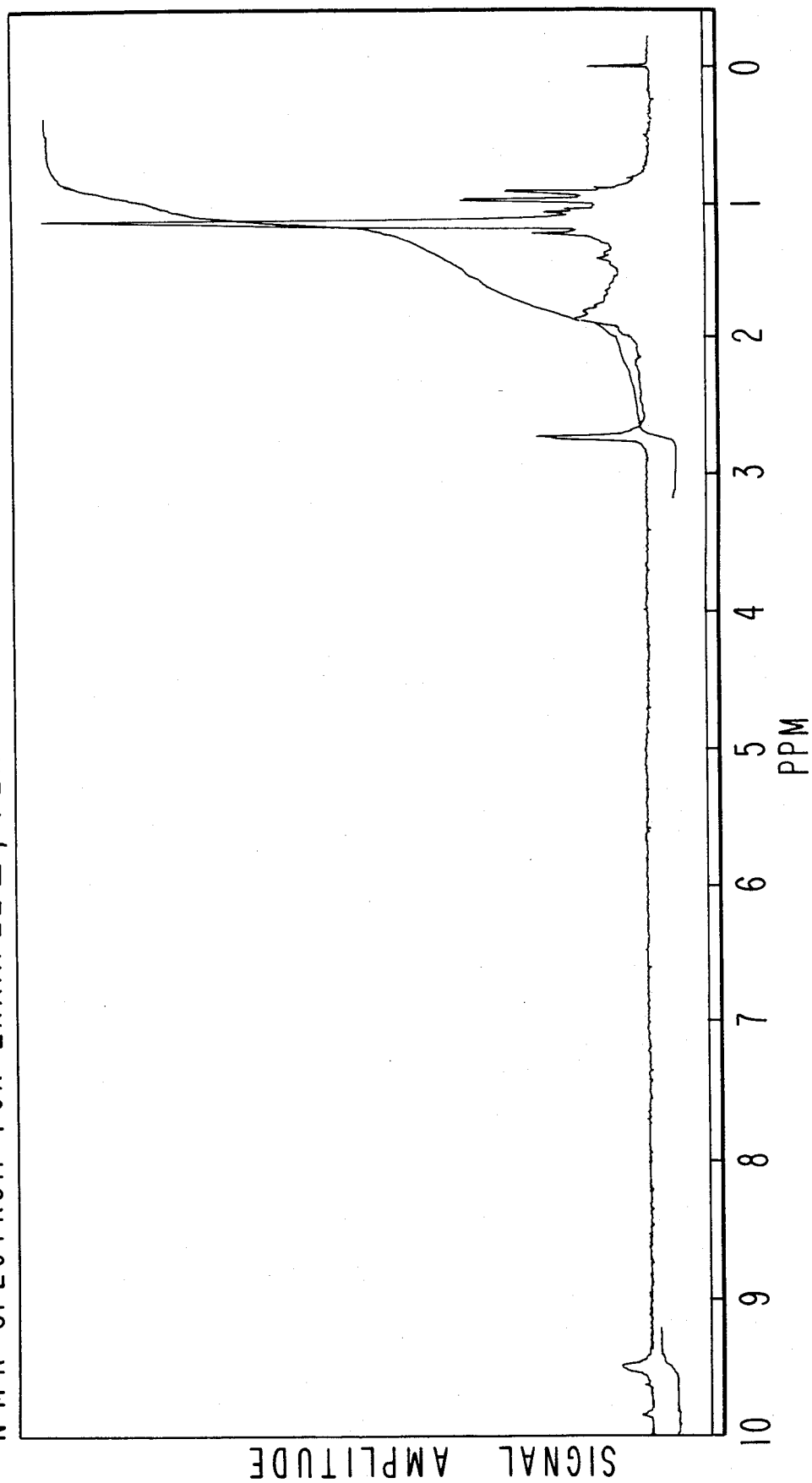

FIG. 2 is the NMR spectrum for the peak indicated by reference numeral "11" of the GLC profile of FIG. 1 for the compound having the structure:

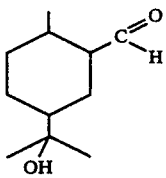

(Conditions: Field strength 100 MHz; Solvent: $CFCl_3$).

Figure 3:
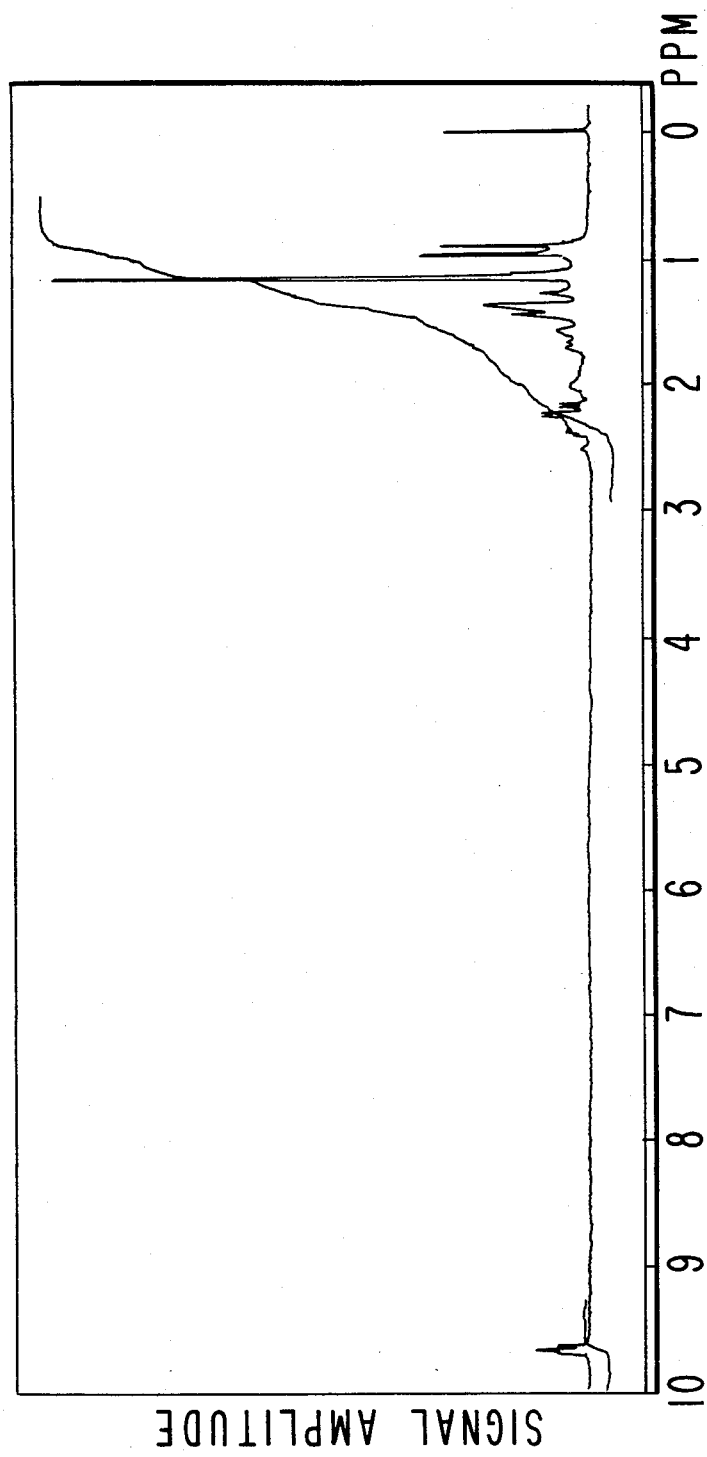

FIG. 3 is the NMR spectrum for the peak indicated by reference numeral "12" of the GLC profile of FIG. 1 for the compound having the structure:

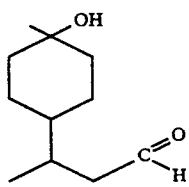

(Conditions: Field strength: 100 MHz; Solvent: $CFCl_3$).

Figure 4:
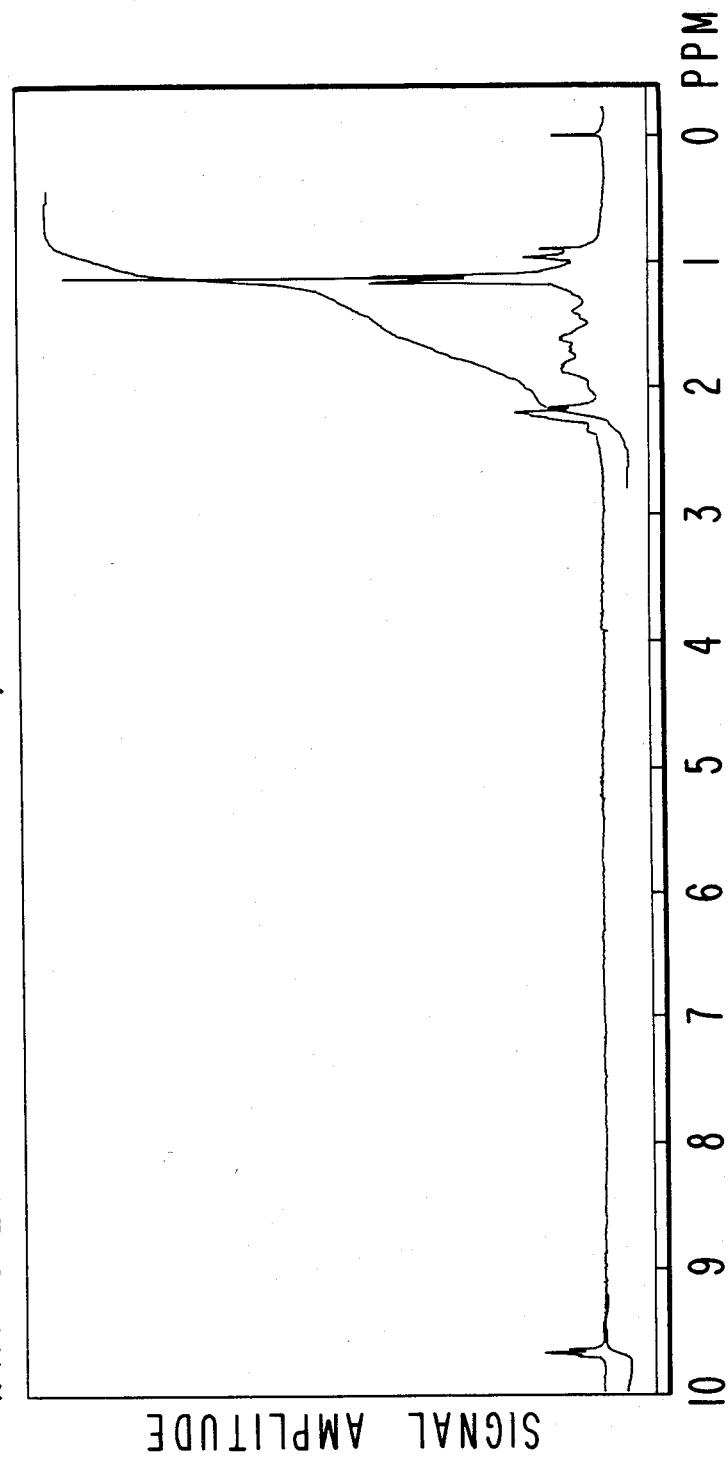

FIG. 4 is the NMR spectrum for the peak indicated by reference numeral "13" of the GLC profile of FIG. 1 containing the compounds having the structures:

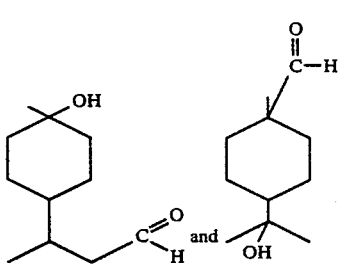

(Conditions: Field strength: 100 MHz; Solvent: $CFCl_3$).

Figure 5:
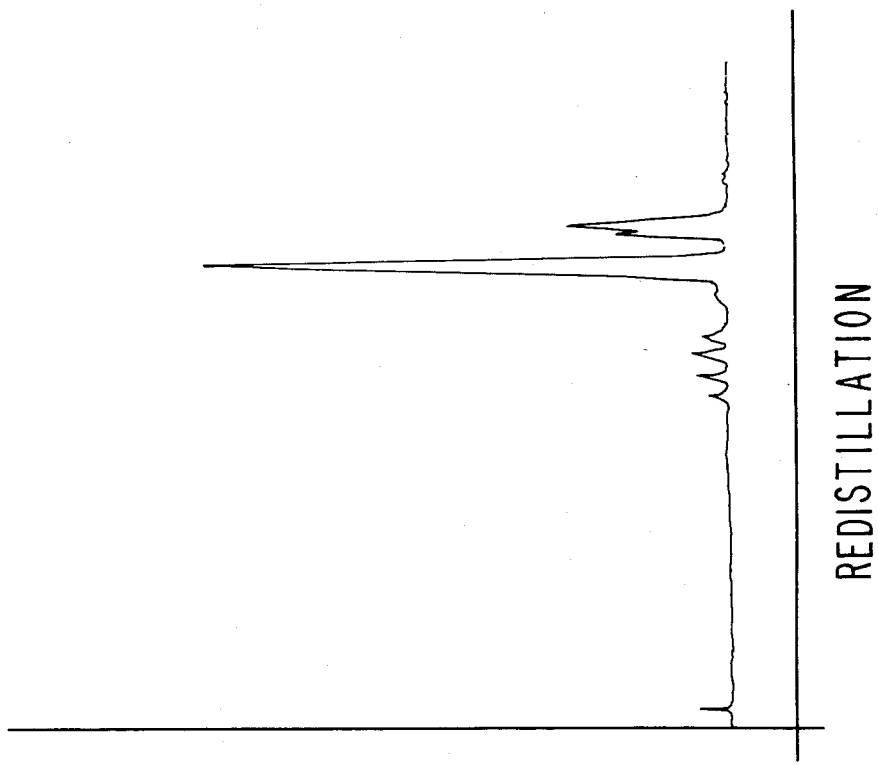

FIG. 5 is the GLC profile for the crude reaction product produced according to Example II containing the compounds having the structures:

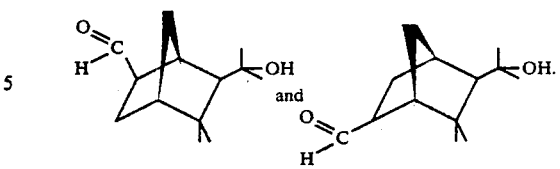

Figure 6:
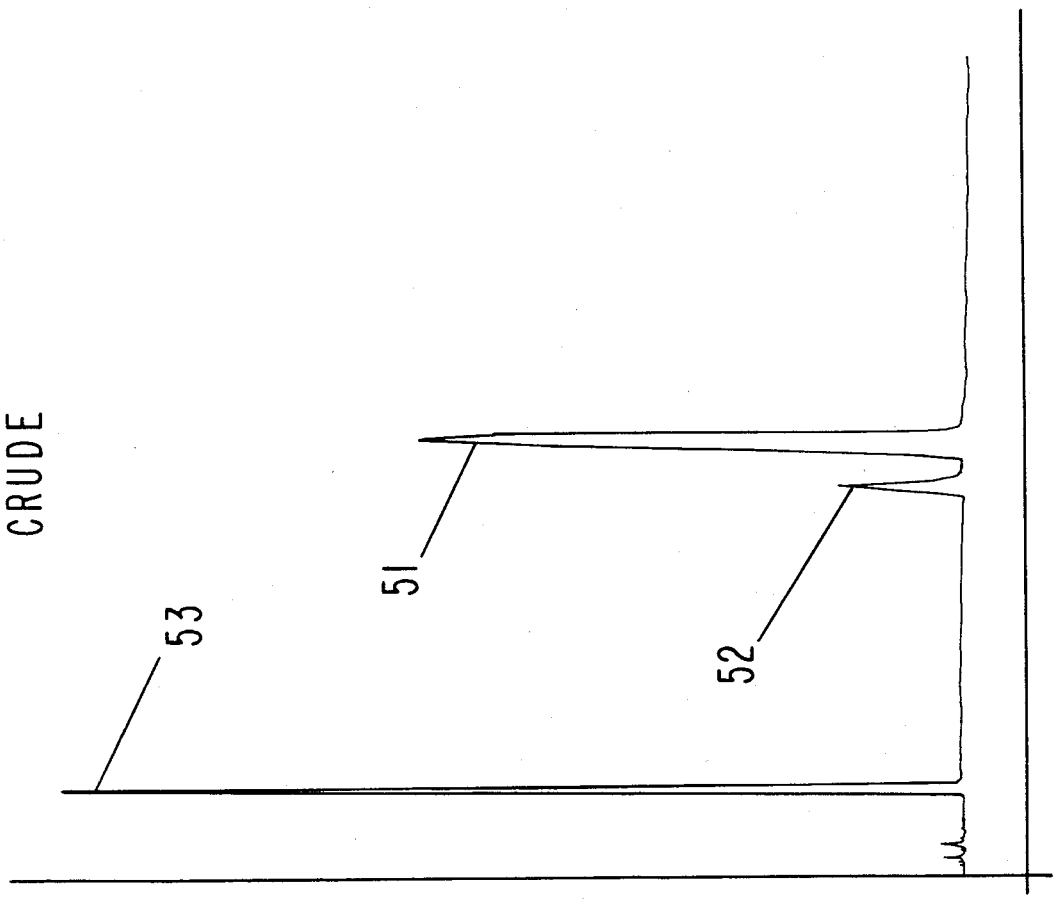

FIG. 6 is the GLC profile for Fraction 1 of the re-distillation product of Example II containing the compounds defined according to the structures:

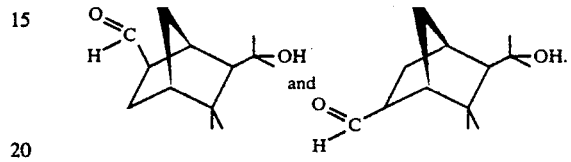

Figure 7:
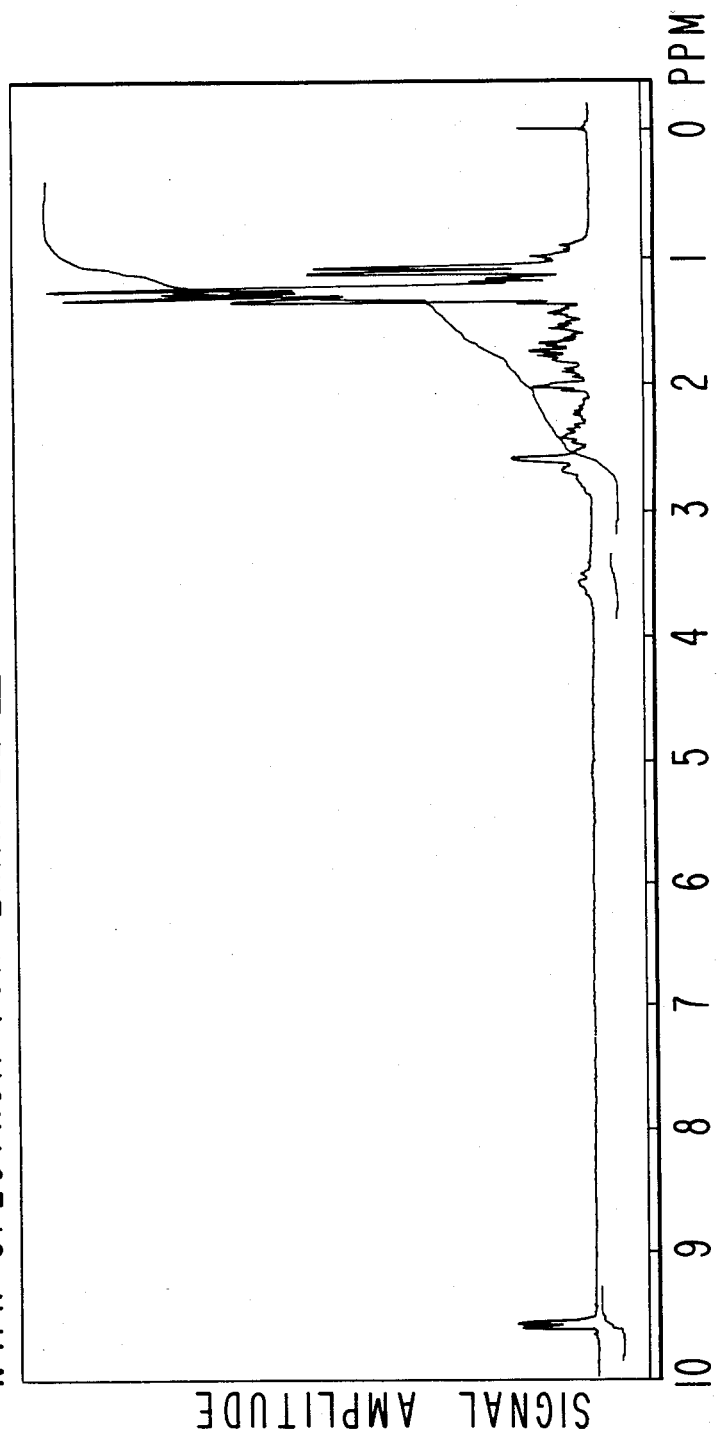

FIG. 7 is the NMR spectrum for a mixture of compounds having the structures:

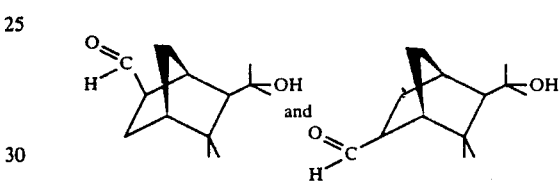

produced according to Example II.
(Conditions: Field strength: 100 MHz; Solvent: $CFCl_3$).

Figure 8:
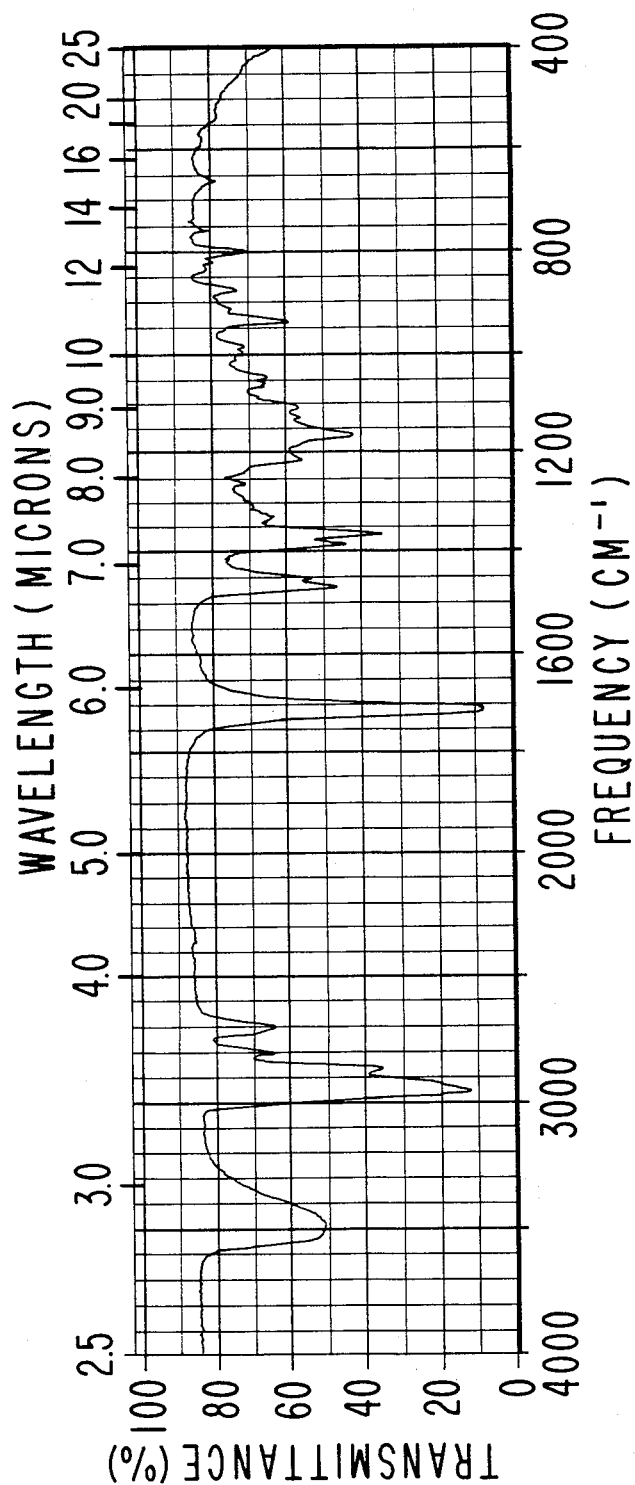

FIG. 8 is the infra-red spectrum for the mixture of compounds having the structures:

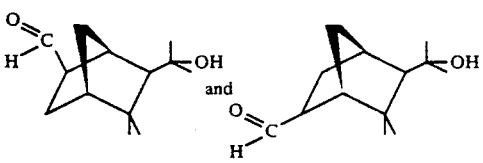

produced according to Example II.

Figure 9:
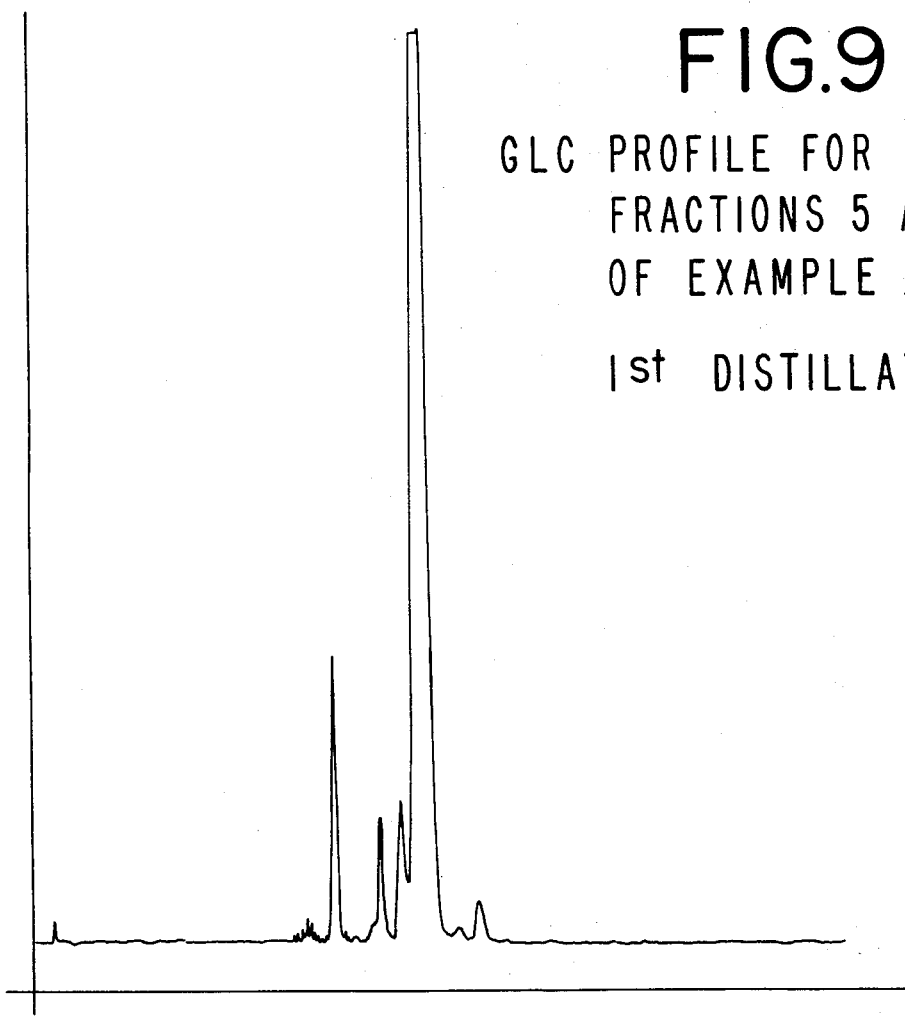

FIG. 9 is the GLC profile for bulked fractions 5 and 6 of the first distillation of the reaction product of Example III containing the compound having the structure:

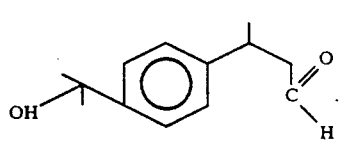

Figure 10:
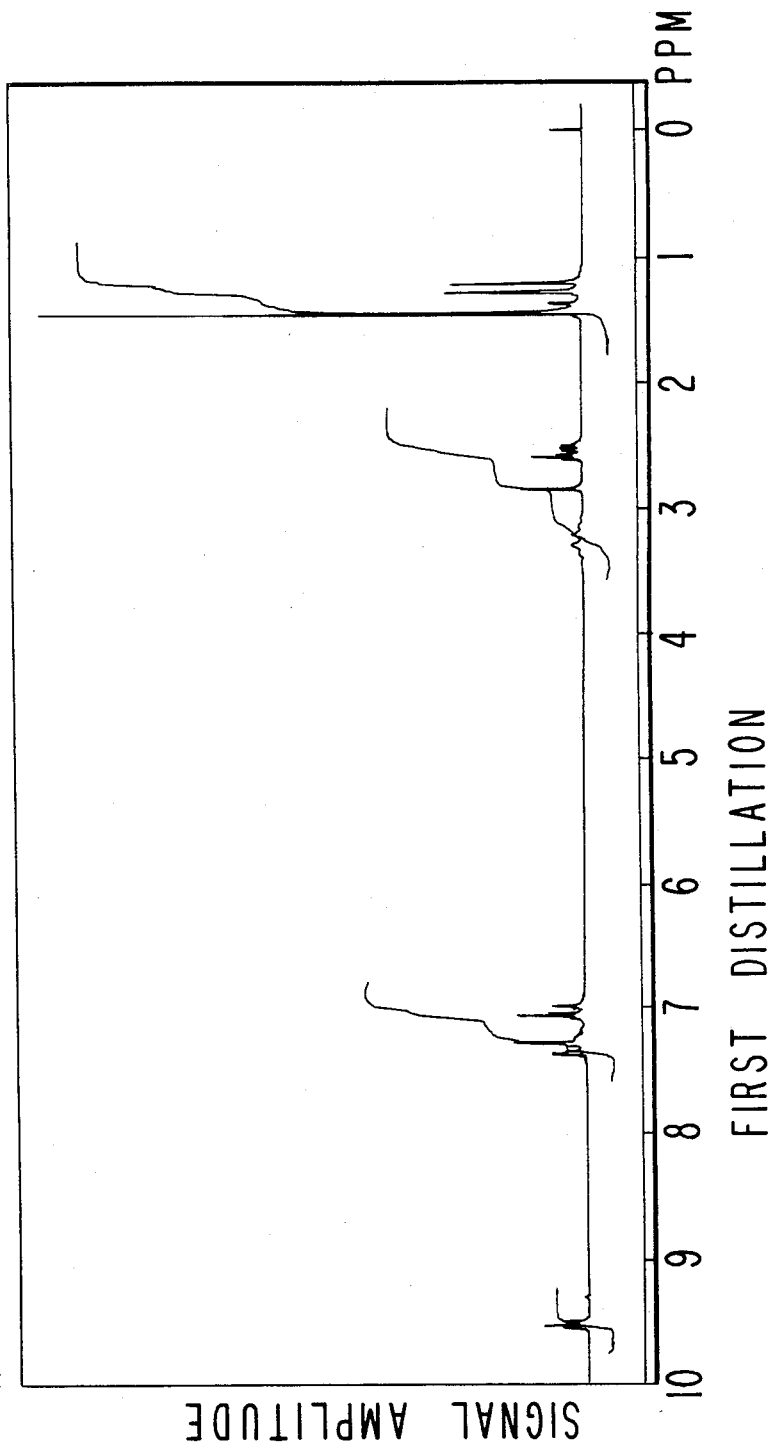

FIG. 10 is the NMR spectrum for Fraction 6 of the first distillation of the reaction product of Example III containing the compound having the structure:

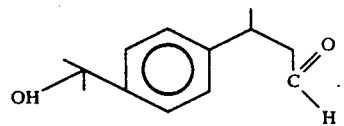

(Conditions: Field strength: 100 MHz; Solvent: CFCl₃).

FIG. 11 is the infra-red spectrum for Fraction 6 of the first distillation of the reaction product of Example III containing the compound having the structure:

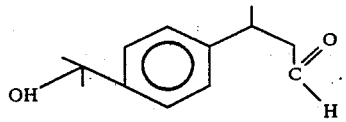

FIG. 12 is the GLC profile for the crude reaction product of Example IV containing the compounds defined according to the structures:

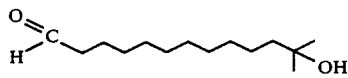

and

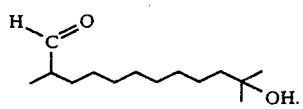

Figure 13:
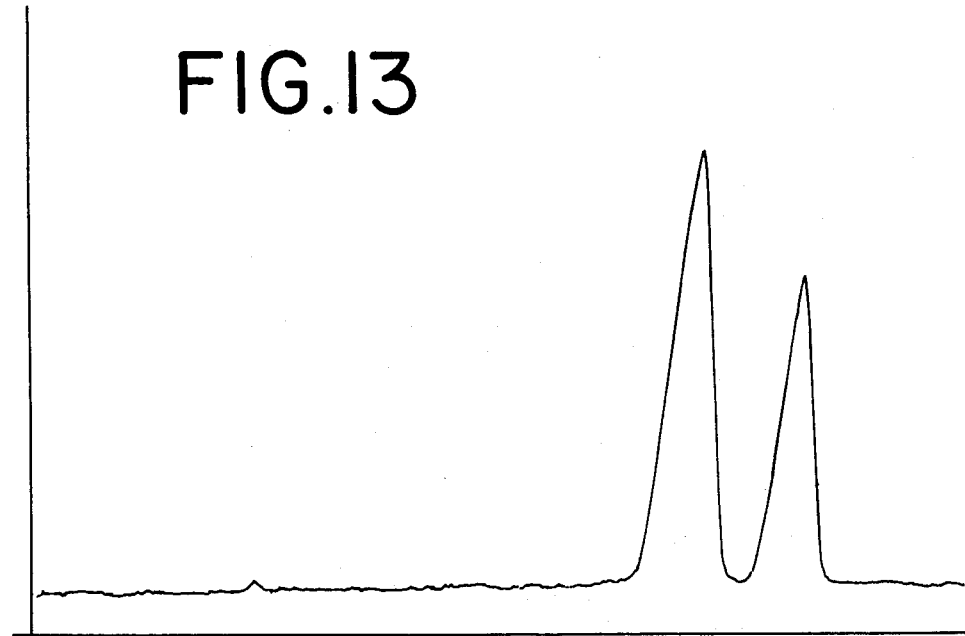

FIG. 13 is the GLC profile for Fraction 6 of the second distillation of Example IV containing the compound having the structure:

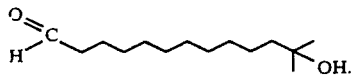

Figure 14:
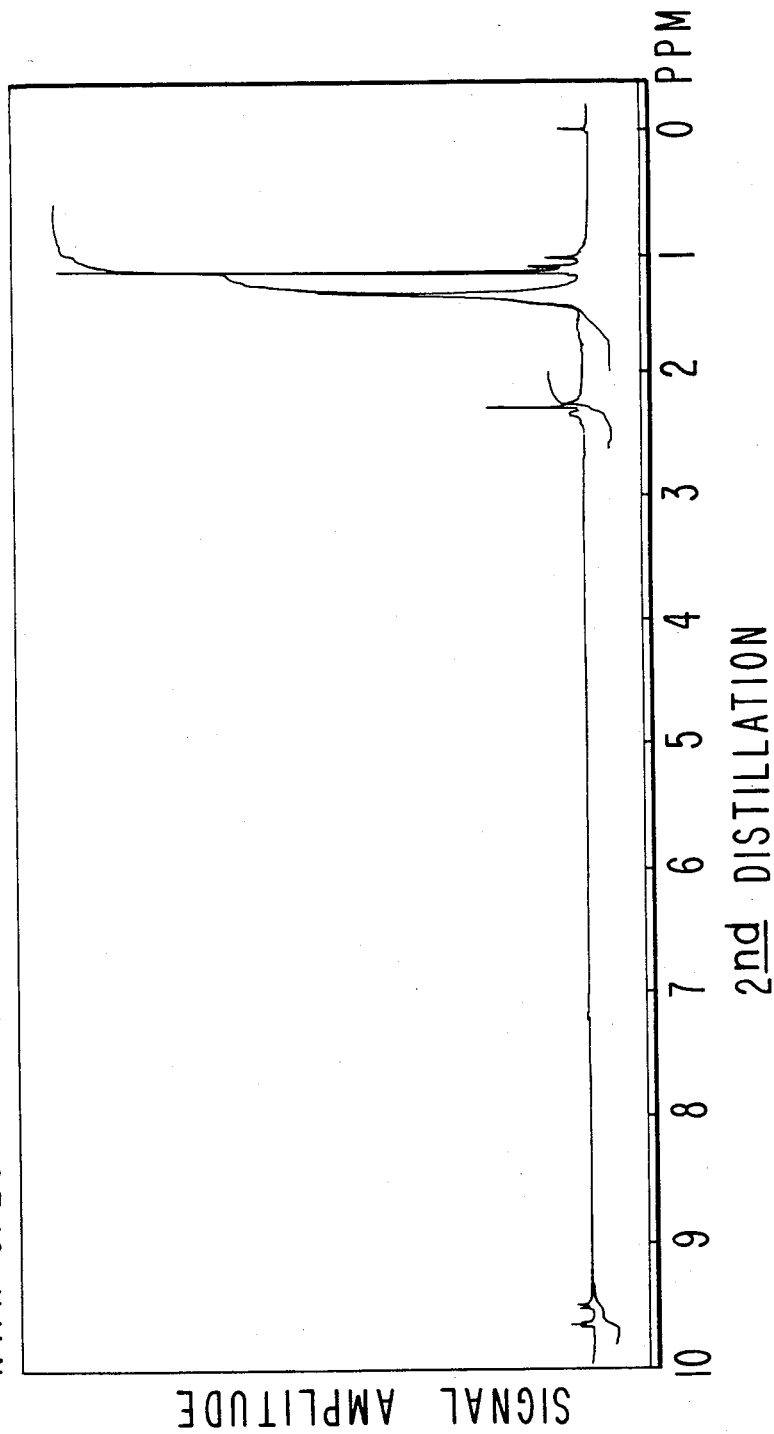

FIG. 14 is the NMR spectrum for Fraction 4 of the second distillation of Example IV containing the compound having the structure:

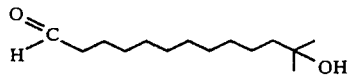

(75%) and the compound having the structure:

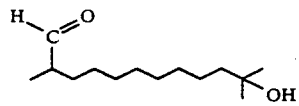

(25%). (Conditions: Field strength: 100 MHz; Solvent: CFCl₃).

DETAILED DESCRIPTION OF THE DRAWINGS

FIG. 1 is the GLC profile for fraction 6 of the distillation product of the reaction product of Example I. The peak indicated by reference numeral "11" is the peak for the compound having the structure:

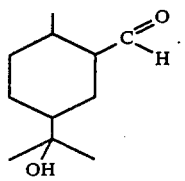

The peak indicated by reference numeral "12" is the peak for the compound having the structure:

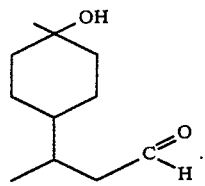

The peak indicated by reference numeral "13" is the peak for the compound having the structure:

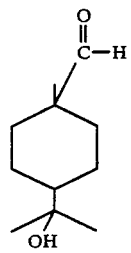

in admixture with the compound having the structure:

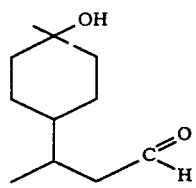

(conditions of GLC operation: Carbowax column programmed at 100°-220° C., isothermal).

FIG. 5 is the GLC profile for the crude reaction product of Example II. The peak indicated by reference numeral "51" is the peak for the mixture of compounds defined according to the structures:

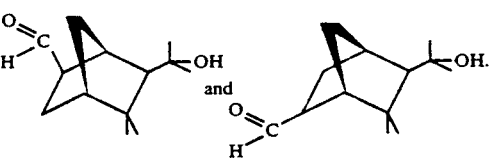

The peak indicated by reference numeral "52" is the peak for the starting material having the structure:

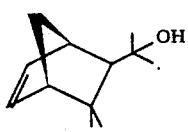

The peak indicated by reference numeral "53" is the peak for the reaction solvent, toluene.

FIG. 12 is the GLC profile for the crude reaction product of Example IV. The peak indicated by reference numerals "122" and "123" are the peaks for the compounds defined according to the structures:

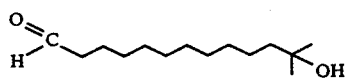

and

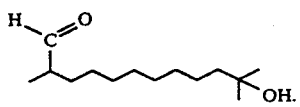

The peak indicated by reference numeral "121" is the peak for the reaction solvent, toluene.

THE INVENTION

It has now been determined that tertiary hydroxyl carboxaldehydes defined according to the generic structure:

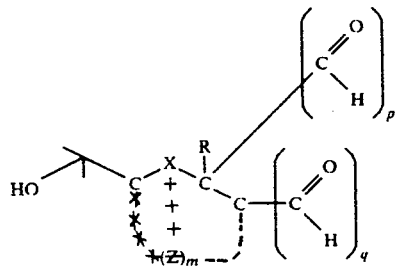

wherein the lines

✳ ✳ ✳ ✳ ✳ and

— — — — — — and/or

+ + + + + represent covalent carbon-carbon bonds when m does not=0; and wherein the lines

+ + + + +

✳ ✳ ✳ ✳ ✳ and

— — — — — — do not represent any bonds when m=0; wherein R represents hydrogen or methyl; wherein p and q each represents 0 or 1 with the proviso that p=1 when q=0 and p=0 when q=1; wherein X and Z each represent one or more carbon atoms required to complete a bicyclo ring with the lines

+ + + + +

✳ ✳ ✳ ✳ ✳ and

— — — — — — representing carbon-carbon bonds; wherein X and Z complete a phenyl moiety when the line

— — — — — — represents no bond; wherein X and z complete a cycloalkyl ring moiety with the lines

✳ ✳ ✳ ✳ ✳ and

+ + + + + represent carbon-carbon bonds and with the line

— — — — — — representing no bond; and wherein when m is 0, X represents an alkylene moiety, are capable of imparting, augmenting or enhancing a variety of fragrances in or to consumable materials.

Briefly, our invention contemplates augmenting or enhancing fragrances of such consumable materials as perfumes, perfumed articles, (e.g., solid or liquid anionic, cationic, nonionic or zwitterionic detergents, cosmetic powders, fabric softener compositions, drier-added fabric softener articles and perfumed polymers) and colognes by adding thereto a small, but effective, amount of at least one of the compounds defined according to the generic structure:

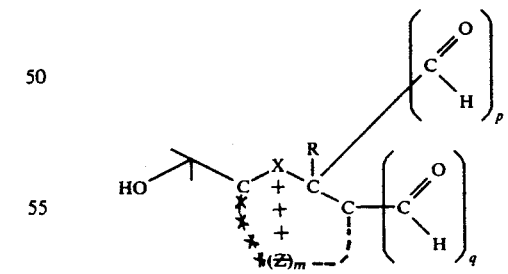

wherein the lines

✳ ✳ ✳ ✳ ✳ and

— — — — — — and/or

+ + + + + represent covalent carbon-carbon bonds when m does not=0; and wherein the lines

+ + + + +

✶ ✶ ✶ ✶ ✶ and

— — — — — do not represent any bonds when m=0; wherein R represents hydrogen or methyl; wherein p and q each represents 0 or 1 with the proviso that p=1 when q=0 and p=0 when q=1; wherein X and Z each represent one or more carbon atoms required to complete a bicyclo ring with the lines

+ + + + +

✶ ✶ ✶ ✶ ✶ and

— — — — — representing carbon-carbon bonds; wherein X and Z complete a phenyl moiety when the line

— — — — — represents no bond; wherein X and Z complete a cycloalkyl ring moiety with the lines

✶ ✶ ✶ ✶ ✶ and

+ + + + + represent carbon-carbon bonds and with the line

— — — — — representing no bond; and wherein when m is 0, X represents an alkylene moiety.

More specifically, the structures of the compounds useful in practicing our invention are as follows:

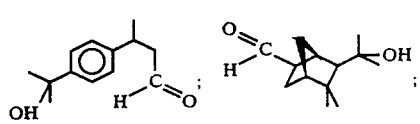

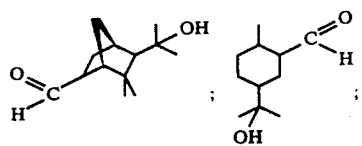

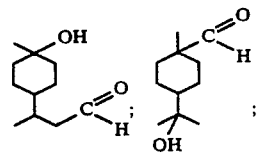

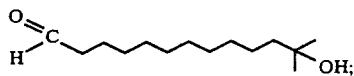

and

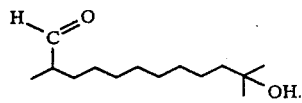

The tertiary hydroxyl carboxaldehydes of our invention augment or enhance woody, nutty, floral, lilac, peach-like, green, balsamic and fresh air dried linen aromas adding thereto minty, floral, cinnamon-like and green topnotes to perfumes, perfumed articles and colognes thereby causing one or more of said tertiary hydroxyl carboxaldehydes to be useful particularly in vetiver type and "fresh air dried linen" type fragrances.

The tertiary hydroxyl carboxaldehydes of our invention may be prepared by first (i) reacting unsaturated compounds defined according to the generic structure:

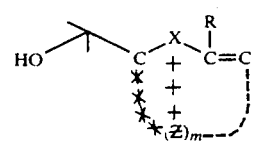

with carbon monoxide and hydrogen in the presence of a "oxo" reaction catalyst according to the reaction:

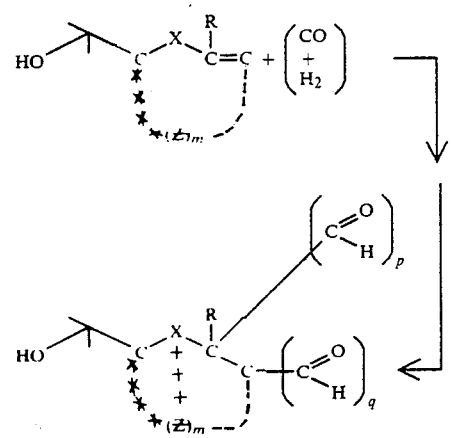

wherein the lines

✶ ✶ ✶ ✶ ✶ and

— — — — — and/or

+ + + + + represent covalent carbon-carbon bonds when m does not=0; and wherein the lines

+ + + + + and

— — — — — do not represent any bonds when m=0; wherein R represents hydrogen or methyl; wherein p and q each represents 0 or 1 with the proviso that p=1 and q=0 and p=0 when q=1; wherein X and Z each represent one or more carbon atoms required to complete a bicyclo ring with the lines

+ + + + +

✳ ✳ ✳ ✳ ✳ and

— — — — — representing carbon-carbon bonds; wherein X and Z complete a phenyl moiety when the line

— — — — — represents no bond; wherein X and Z complete a cycloalkyl ring moiety with the lines

✳ ✳ ✳ ✳ ✳ and

+ + + + + represent carbon-carbon bonds and with the line

— — — — — representing no bond; and wherein when m is 0, X represents an alkylene moiety. The reaction is carried out at temperatures of between 110° C. and 300° C. at pressures of between 15 and 250 atmospheres; with the ratio of partial pressure of carbon monoxide:hydrogen being from 0.1:1 up to 1:0.1. Any oxo type reaction catalyst may be used, but, most preferably, the catalyst to yield the best perfume mixtures are as follows:

Dicobalt octacarbonyl;
Cobalt octanoate;
Palladium chloride;
Rhodium trichloride;
Iron pentacarbonyl;
Nickel tetracarbonyl;
Polymer-bonded rhodium catalyst (e.g., rhodium bonded on a polystyrene substrate);
Tris-triphenyl phosphine rhodium-1-chloride;
Rhodium acetoacetate dicarbonyl;
Rhodium-acetoacetate-triphenylphosphene.

Depending upon the conditions of reaction including, temperature, partial pressures of carbon monoxide and hydrogen, mole ratio of alcohol having the structure:

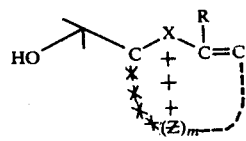

to catalyst, concentration of alcohol having the structure:

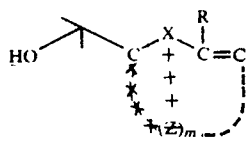

in solvent, concentration of catalyst in solvent and time of reaction, the nature of the isomers of the aldehydes defined according to the structure:

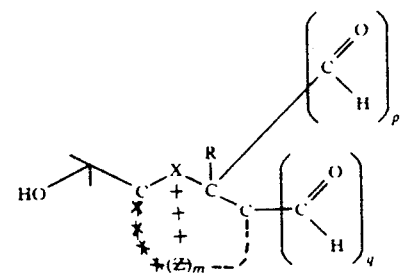

wherein the lines

✳ ✳ ✳ ✳ ✳ and

— — — — — and/or

+ + + + + represent covalent carbon-carbon bonds when m does not=0; and wherein the lines

+ + + + +

✳ ✳ ✳ ✳ ✳ and

— — — — — do not represent any bonds when m=0; wherein R represents hydrogen or methyl; wherein p and q each represents 0 or 1 with the proviso that p=1 when q=0 and p=0 when q=1; wherein X and Z each represent one or more carbon atoms required to complete a bicyclo ring with the lines

+ + + + +

✳ ✳ ✳ ✳ ✳ and

— — — — — representing carbon-carbon bonds; wherein X and Z complete a phenyl moiety when the line

— — — — — represents no bond; wherein X and Z complete a cycloalkyl ring moiety with the lines

* * * * and

+ + + + + represent carbon-carbon bonds and with the line representing no bond; and wherein when m is 0, X represents an alkylene moiety will vary. The variation of the conditions of reaction is a function of the nature of the perfumery product desired. Accordingly, the organoleptic qualities of the product desired can be varied in a tailor-made fashion as a function of the conditions of the reaction.

Exemplary of the reactants and products produced in their organoleptic properties are the following:

TABLE I

| Alcohol Reaction | Aldehyde Reaction Product | Organoleptic Property |
|---|---|---|
| 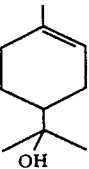 | Mixture of compounds having the structures: 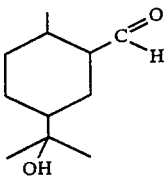 and 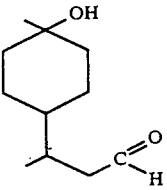 | A woody and nutty aroma with minty and floral topnotes. |
| 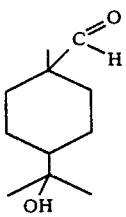 | Mixture of compounds having the structures: 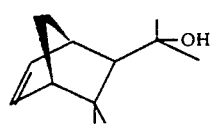 and  | A floral (lilac) aroma with cinnamon-like topnotes. |
| 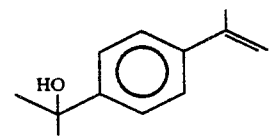 | The compound having the structure: 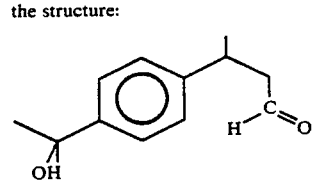 | A green, woody, peach-like and balsamic aroma profile with green floral topnotes. |

TABLE I-continued

| Alcohol Reaction | Aldehyde Reaction Product | Organoleptic Property |
|---|---|---|
| 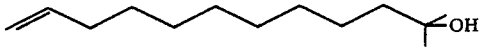 | A mixture of compounds having the structures:<br>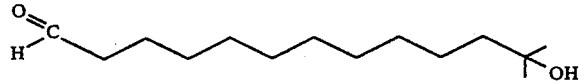<br>and<br>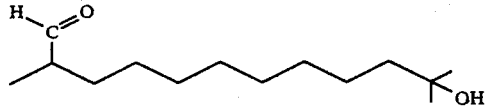 | A fresh air dried linen aroma. |

As olfactory agents, the tertiary hydroxyl carboxaldehydes taken alone or in admixture, of our invention, can be formulated into, or used as components of a "perfume composition" or can be used as components of a "perfumed article", or the perfume composition may be added to perfumed articles.

The term "perfume composition" is used herein to mean a mixture of organic compounds including, for example, mono alcohols, aldehydes (other than the tertiary hydroxyl carboxaldehydes of our invention), ketones, nitriles, ethers, lactones, natural essential oils, synthetic essential oils and hydrocarbons which are admixed so that the combined odors of the individual components produce a pleasant or desired fragrance. Such perfume compositions usually contain (a) the main note or the "bouquet" or foundation stone of the compositions; (b) modifiers which round off and accompany the main note; (c) fixatives which include odorous substances which lend a particular note to the perfume throughout all stages of evaporation, and substances which retard evaporation; and (d) topnotes which are usually low boiling, fresh-smelling materials.

In perfume compositions, the individual component will contribute its particular olfactory characteristics, but the overall effect of the perfume composition will be the sum of the effects of each of the ingredients and in certain instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the tertiary hydroxyl carboxaldehydes of our invention which will be effective in perfume compositions depends on many factors, including the other ingredients, their amounts and the effects which are desired. It has been found that perfume compositions containing as little as 0.05% of the tertiary hydroxyl carboxaldehydes of this invention, or even less, can be used to impart an interesting, woody, nutty, floral, lilac, green, peach-like, balsamic and fresh air dried linen aromas with minty, floral, cinnamon-like and green topnotes to soaps, liquid or solid anionic, cationic, nonionic or zwitterionic detergents, cosmetics, cosmetic powders, liquid and solid fabric softeners, drier-added fabric softener articles, (e.g., BOUNCE ® a registered trademark of the Procter & Gamble Company of Cincinnati, Ohio), optical brightener compositions and other products. The amount employed can range up to 70% or even higher, and will depend on considerations of cost, nature of the end product, and the effect desired on the finished product and particular fragrance sought. Thus, for example, when fragrancing liquid bleach compositions containing alkalihypochlorite such as, for example, sodium hypochlorite, for example CLOROX ®, (registered trademark of Clorox, Inc.), the amount employed can be as high as 100% of the fragrance involved in the liquid bleach. Indeed, a distinctive aspect of our invention is the use of one or more of the tertiary hydroxyl carboxaldehydes of our invention in a stable liquid bleach composition.

The tertiary hydroxyl carboxaldehydes of this invention, taken alone or in admixture, can be used alone, or in a perfume composition as an olfactory component in detergents, soaps, space odorants and deodorants; perfumes; colognes, toilet waters; bath salts; hair preparations, such as lacquers, brilliantines, pomades and shampoos; cosmetic preparations, such as creams, deodorants, hand lotions, sunscreens; powders, such as talcs, dusting powders, face powders and the like; liquid bleaches, such as sodium hypochlorite-containing bleaches; floor waxes; automobile aromas and automobile polish compositions; and perfumed polymers and perfumed polymer articles of manufacture such as perfumed garbage bags.

When used as an olfactory component of a perfumed article, as little as 0.01% of one or more of the tertiary hydroxyl carboxaldehydes of our invention will suffice to impart an interesting, woody, nutty, floral, lilac, green, peach-like, balsamic and fresh air dried linen aromas with minty, floral, cinnamon-like and green topnotes. Generally, no more than 0.5% is required to impart such aromas, however, in view of the rather low cost of the tertiary hydroxyl carboxaldehydes of our invention, up to 100% of the perfume composition can be one or more of the tertiary hydroxyl carboxaldehydes of our invention.

Accordingly, the range of use in perfumed articles of the tertiary hydroxyl carboxaldehydes of our invention is from about 0.01% up to about 0.5%.

In addition, the perfume composition of our invention can contain a vehicle or carrier for the tertiary hydroxyl carboxaldehydes taken alone, or taken together with other ingredients. The vehicle can be a liquid such as a non-toxic alcohol such as ethanol, a glycol such as propylene glycol, or the like. The carrier can be an absorbent solid, such as a gum or components (e.g., gum arabic, xanthan gum or guar gum or combinationa thereof) or components for encapsulating the composition such as gelatin which can be used to form a capsule wall surrounding the perfume oil, as by means of coacervation, or a polymer such as the ureformaldehyde polymer which can be used to surround a perfume liquid center.

It will thus be apparent that the tertiary hydroxyl carboxaldehydes of our invention can be utilized to alter, modify or enhance sensory properties, particularly organoleptic properties such as fragrances of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF 8-HYDROXY-p-METHANE-2-CARBOXALDEHYDE

Reaction:

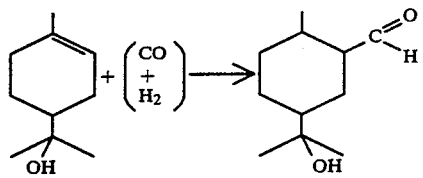

Into a high pressure autoclave is placed 1232 grams (8 moles) of terpinol having the structure:

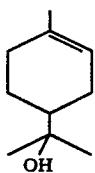

and 0.45 grams of rhodium aceto acetate-dicarbonyl. The autoclave is sealed and pressurized to 1000 psig and heated to a temperature of 150°–160° C. with a 50:50 mole:mole mixture of carbon monoxide and hydrogen. The autoclave contents are maintained at a pressure of 1000 psig and a temperature in the range of 150°–160° C. for a period of forty one hours.

At the end of this time period, the autoclave contents are cooled and the contents are removed from the autoclave filtered and distilled on a 1″ splash column yielding the following fractions:

| Fraction No. | Vapor Temp. (°C.) | Liquid Temp. (°C.) | Vacuum mm/Hg. Pressure |
|---|---|---|---|
| 1 | /74 | /100 | 4:0 |
| 2 | 88 | 110 | 5:5 |
| 3 | 94 | 115 | 5:5 |
| 4 | 105 | 130 | 5:5 |
| 5 | 128 | 130 | 5:5 |
| 6 | 124 | 158 | 2:6 |
| 7 | 149 | 220 | 2:6 |

Fractions 2–7 are bulked and redistilled on an 18″ Goodloe column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 78/83 | 118/124 | 3:2/3:3 | 11.2 |
| 2 | 82 | 127 | 2:7 | 14.9 |
| 3 | 83 | 129 | 2:7 | 12.5 |
| 4 | 83 | 135 | 3:6 | 14.1 |
| 5 | 119 | 135 | 3:0 | 25.3 |
| 6 | 123 | 137 | 3:0 | 25.8 |
| 7 | 123 | 137 | 3:0 | 6.7 |
| 8 | 128 | 144 | 3:0 | 12.1 |
| 9 | 128 | 145 | 3:2 | 9.6 |
| 10 | 127 | 150 | 3:2 | 19.9 |
| 11 | 130 | 162 | 3:4 | 15.0 |
| 12 | 131 | 181 | 3:8 | 8.5 |
| 13 | 128 | 188 | 3:6 | 2.4 |

Fractions 8–10 are bulked and determined to have a woody and nutty aroma with minty and floral topnotes.

FIG. 1 is the GLC profile of Fraction 6 of the foregoing distillation. (Conditions: Carbowax column programmed at 100°–220° C. isothermal). The peak indicated by reference numeral "11" is the peak for the compound having the structure:

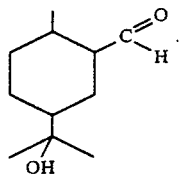

The peak indicated by reference numeral "12" is the peak for the compound having the structure:

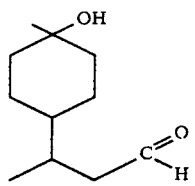

The peak indicated by reference numeral "13" is the peak for the mixture of compounds defined according to the structure:

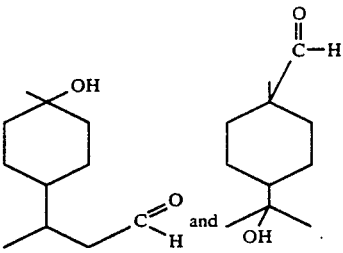

FIG. 2 is the NMR spectrum for the peak indicated by reference numeral "11" on FIG. 1 for the compound defined according to the structure:

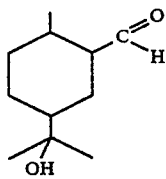

(conditions: Field strength: 100 MHz; Solvent: CFCl₃).

FIG. 3 is the NMR spectrum for the peak indicated by reference numeral "12" on the GLC profile of FIG. 1 for the compound having the structure:

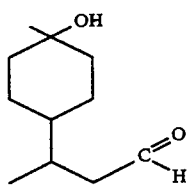

(conditions: Field strength: 100 MHz; Solvent, CFCl₃).

FIG. 4 is the NMR spectrum for the peak indicated by reference numeral "13" on the GLC profile of FIG. 1 and is for a mixture of compounds defined according to the structures:

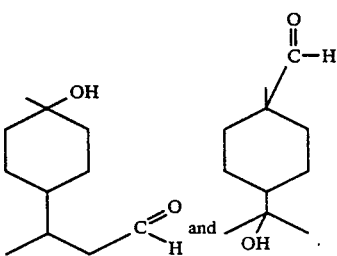

EXAMPLE II

PREPARATION OF 5-(1-HYDROXY-1-METHYLETHYL)-6,6-DIMETHYL-(1 and 2) NORBORNANE CARBOXALDEHYDE Reaction:

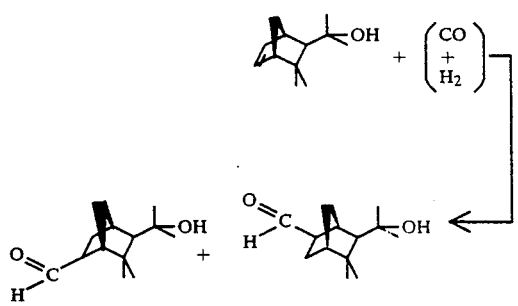

Into a 500 cc autoclave is placed 205.5 grams of the compound having the structure:

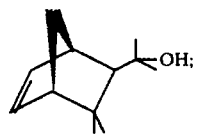

0.1 grams of rhodium aceto acetate and 7 grams of triphenyl phosphine, and 100 cc toluene.

The autoclave is sealed and pressurized to 1000 psig and heated to a temperature of 120° C. using a 50:50 mole:mole mixture of carbon monoxide and hydrogen. The autoclave contents are maintained at 1000 psig and 120° C. for a period of four hours.

At the end of the four hour period, the autoclave contents are cooled and the autoclave is opened and the contents are filtered and then distilled through a 2" splash column yielding the following fractions:

| Fraction No. | Vapor Temp. (°C.) | Liquid Temp. (°C.) | Vacuum mm/Hg. Pressure |
|---|---|---|---|
| 1 | 26/94 | 48/129 | 1:8/0:75 |
| 2 | 99 | 129 | 0:7 |
| 3 | 125 | 139 | 2:1 |
| 4 | 104 | 138 | 0:55 |
| 5 | 132 | 142 | 2:1 |
| 6 | 126 | 198 | 2:2 |

Fractions 2–6 are then bulked and redistilled on an 18" Goodloe column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 128/135 | 147/148 | 3:5/3:6 | 8.1 |
| 2 | 137 | 149 | 3:3 | 14.1 |
| 3 | 140 | 150 | 3:7 | 13.4 |
| 4 | 140 | 149 | 3:4 | 15.0 |
| 5 | 140 | 152 | 3:4 | 31.2 |
| 6 | 140 | 150 | 3:4 | 15.9 |
| 7 | 140 | 150 | 3:4 | 26.4 |
| 8 | 140 | 154 | 3:4 | 19.7 |
| 9 | 140 | 175 | 3:4 | 13.4 |
| 10 | 135 | 230 | 3:4 | 10.3 |

Fractions 5–8 are bulked and the bulked fractions have a floral (lilac) aroma with cinnamon-like topnotes.

FIG. 5 is the GLC profile for the crude reaction product prior to distillation. The peak indicated by reference numeral "51" is the peak for the mixture of compounds defined according to the structures:

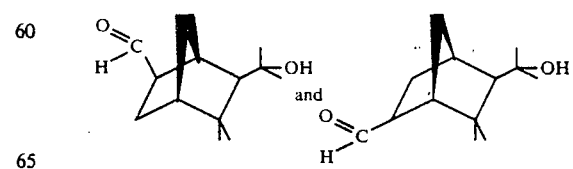

The peak indicated by reference numeral "52" is the peak for the starting material having the structure:

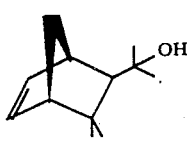

The peak indicated by reference numeral "53" is the peak for the reaction solvent, toluene.

FIG. 6 is the GLC profile for Fraction 1 of the redistillation.

FIG. 7 is the NMR spectrum for the mixture of compounds having the structures:

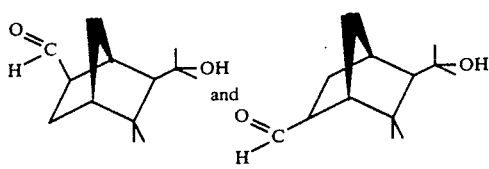

produced according to this example. (Conditions: Field strength: 100 MHz; Solvent: CFCl₃).

FIG. 8 is the infra-red spectrum for the mixture of compounds having the structures:

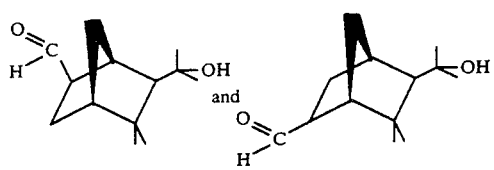

produced according to this example.

EXAMPLE III

PREPARATION OF
p-(1-HYDROXY-1-METHYLETHYL)-β-METHYL-HYDROCINNAMALDEHYDE

Reaction:

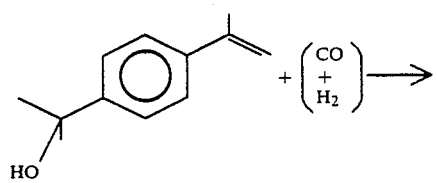

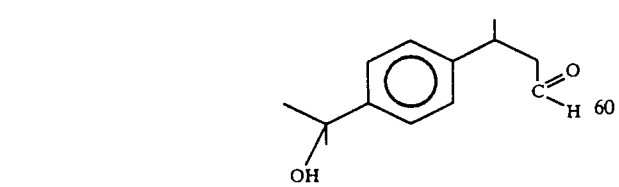

Into a 700 cc autoclave is placed the following ingredients:

(i) 110 grams p-isopropyl phenyl dimethyl carbinol having the structure:

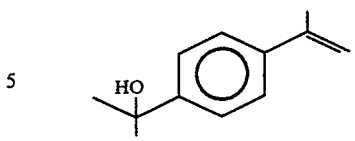

(ii) 8 grams—triphenyl phosphine;
(iii) 0.1 grams—rhodium aceto acetate;
(iv) 300 ml—toluene The autoclave is closed and pressured with a 50:50 mole:mole mixture of carbon monoxide and hydrogen to a pressure of 1000 psig and heated to a temperature in the range of 120°–150° C. and maintained at 120°–150° C. and at a pressure of 1000 psig for a period of fifteen hours.

At the end of the fifteen hour period, the autoclave is cooled and opened and the contents are filtered. The resulting filtrate is then distilled through a 6" Miller column yielding the following fractions:

| Fraction No. | Vapor Temp. (°C.) | Liquid Temp. (°C.) | Vacuum mm/Hg. Pressure |
|---|---|---|---|
| 1 | /24 | /27 | 1:0 |
| 2 | 24 | 31 | 2:1 |
| 3 | 25 | 87 | 1:0 |
| 4 | 108 | 152 | 0:5 |
| 5 | 122 | 154 | 0:5 |
| 6 | 130 | 200 | 0:5 |

Fractions 5–6 are bulked and redistilled on an 18" Goodloe column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | /65 | /165 | 2:3 | 2.5 |
| 2 | 94 | 156 | 2:3 | 5.7 |
| 3 | 55 | 158 | 2:4 | 5.3 |
| 4 | 80 | 156 | 2:3 | 7.4 |
| 5 | 82 | 157 | 2:2 | 7.9 |
| 6 | 113 | 163 | 2:0 | 8.6 |
| 7 | 120 | 168 | 2:0 | 12.0 |
| 8 | 106 | 187 | 2:0 | 7.3 |
| 9 | 53 | 200 | 2:0 | 9.4 |

Fractions 5–8 are bulked. The bulked fractions have an interesting green, woody, peach-like and balsamic aroma profile with green and floral topnotes.

FIG. 9 is the GLC profile of bulked Fractions 5–6 of the first distillation.

FIG. 10 is the NMR spectrum for Fraction 6 of the first distillation containing the compound having the structure:

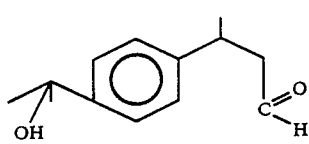

(conditions: Field strength: 100 MHz; Solvent: CFCl₃).

FIG. 11 is the infra-red spectrum for Fraction 6 of the first distillation containing the compound having the structure:

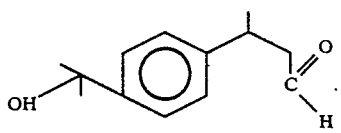

EXAMPLE IV

PREPARATION OF 12-HYDROXY-12-METHYL TRIDECANAL

Reaction:

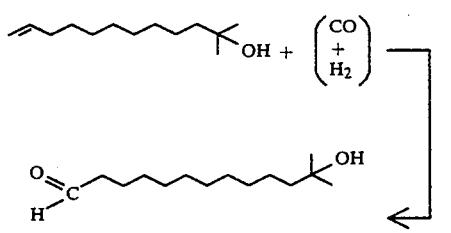

Into a 1000 cc autoclave is placed the following ingredients:
(i) 302 grams of the alcohol having the structure:

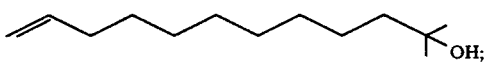

(ii) 0.1 grams of rhodium aceto acetate;
(iii) 6.5 grams of triphenylphosphine;
(iv) 200 ml—toluene.

The autoclave is sealed and the pressure is increased to 700 psig using a 50:50 mole:mole mixture of carbon monoxide and hydrogen. The temperature of the contents is raised to a 120°–140° C. and maintained at a temperature of 120°–140° C. at a pressure of 700 psig for a period of twenty five hours. At the end of the twenty five hour period, the autoclave is cooled and the contents are filtered. The filtrate is then distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | /132 | /160 | 3:6 | 1.3 |
| 2 | 154 | 167 | 4:8 | 26.8 |
| 3 | 150 | 162 | 3:0 | 96.7 |
| 4 | 152 | 162 | 1:6 | 77.3 |
| 5 | 152 | 260 | 3:0 | 101.6 |

Fractions 2–5 are bulked and redistilled on a 18" Goodloe column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 142/ | 160/ | 2:0 | 7.2 |
| 2 | 145 | 162 | 7:0 | 23.8 |
| 3 | 146 | 162 | 2:0 | 30.5 |
| 4 | 146 | 163 | 2:0 | 30.2 |
| 5 | 146 | 165 | 2:0 | 29.3 |
| 6 | 146 | 167 | 2:0 | 19.0 |
| 7 | 146 | 170 | 2:0 | 21.4 |
| 8 | 146 | 180 | 2:0 | 18.6 |
| 9 | 146 | 195 | 2:0 | 13.4 |
| 10 | 144 | 230 | 2:0 | 9.9 |
| 11 | 140 | 245 | 2:0 | 3.4 |

Fractions 4–8 of the foregoing distillation are bulked and have a fresh air dried linen aroma.

FIG. 12 is the GLC profile for the crude reaction product prior to the first distillation. The peaks indicated by reference numerals "122" and "123" are the peaks for the compounds defined according to the structures:

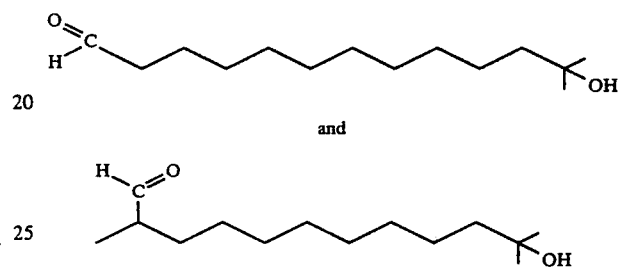

The peak indicated by reference numeral "121" is the peak for the toluene solvent used in the reaction mass.

FIG. 13 is the GLC profile for Fraction 6 of the second distillation.

FIG. 14 is the NMR spectrum for Fraction 4 of the second distillation (conditions: Field strength: 100 MHz; Solvent: CFCl$_3$). This material contains 25% by weight of the compound having the structure:

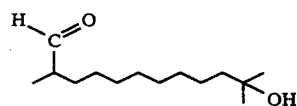

and 75% by weight of the compound having the structure:

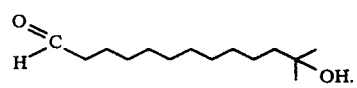

EXAMPLE V

PREPARATION OF PINE FORMULATION

The following pine formulations are prepared:

| Ingredient | V-A | V-B | V-C | V-D |
|---|---|---|---|---|
| Isoburnyl acetate | 100 | 100 | 100 | 100 |
| Camphor | 10 | 10 | 10 | 10 |
| Terpineol | 25 | 25 | 25 | 25 |
| Fir balsam absolute (50% in diethyl phthalate) | 20 | 20 | 20 | 20 |
| Coumarin | 4 | 4 | 4 | 4 |
| Linalool | 30 | 30 | 30 | 30 |
| Anethol | 2 | 2 | 2 | 2 |
| Fenchyl alcohol | 10 | 10 | 10 | 10 |
| Lemon terpenes washed | 50 | 50 | 50 | 50 |
| Borneol | 5 | 5 | 5 | 5 |
| Galbanum oil | 5 | 5 | 5 | 5 |
| Turpentine Russian | 150 | 150 | 150 | 150 |
| *Pinus pumilionus* | 50 | 50 | 50 | 50 |
| Eucalyptol | 50 | 50 | 50 | 50 |

-continued

| Ingredient | V-A | V-B | V-C | V-D |
|---|---|---|---|---|
| 2,2,6-trimethyl-1-cyclohexene-1-carboxaldehyde | 5 | 5 | 5 | 5 |
| Maltol (1% in diethyl phthalate) | 5 | 5 | 5 | 5 |
| Bulked Fractions 8–10 of the distillation product of Example I containing the compounds having the structures: 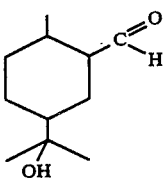 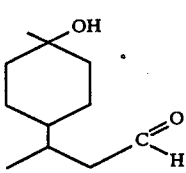 and 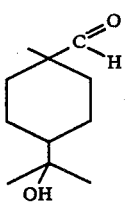 | 479 | 000 | 000 | 000 |
| Mixture of compounds having the structures: 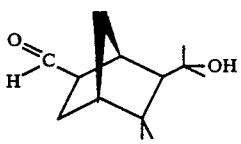 and 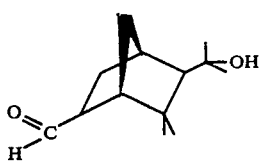 produced according to Example II, bulked Fractions 5–8 | 0 | 479 | 0 | 0 |
| Compound having the structure: 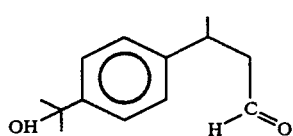 produced according to Example III, bulked Fractions 5–8 | 0 | 0 | 479 | 0 |
| Mixture of compounds having the structures: | 0 | 0 | 0 | 479 |

-continued

| Ingredient | V-A | V-B | V-C | V-D |
|---|---|---|---|---|

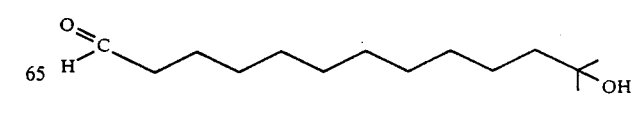

and

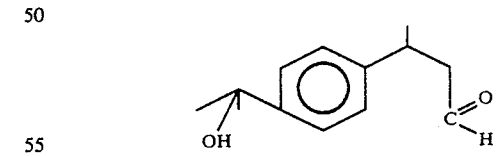

prepared according to Example IV, bulked distillation Fractions 4–8

The perfume formulation containing the mixture of compounds having the structures:

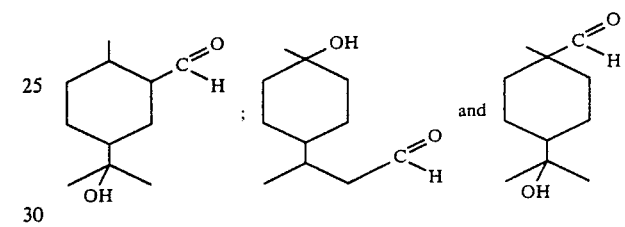

can be described as "piney having woody and nutty undertones and minty and floral topnotes".

The formulation containing the mixture of compounds defined according to the structures:

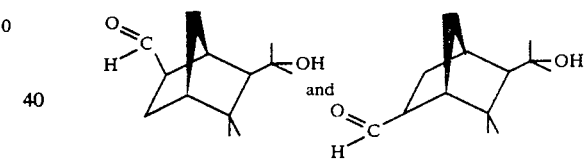

produced according to Example II can be described as "piney having lilac undertones and floral (lilac-like) and cinnamon-like topnotes".

The formulation containing the compound having the structure:

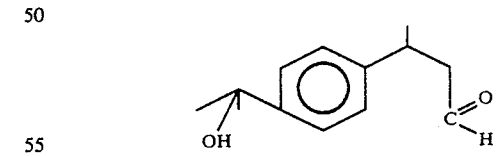

produced according to Example III can be described as "piney with green, woody, peach-like and balsamic undertones and green, floral topnotes".

The formulation containing the mixture of compounds having the structures:

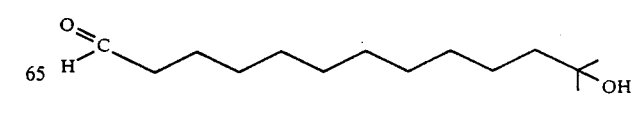

and

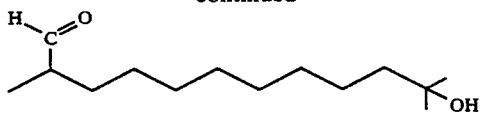

produced according to Example IV can be described as "piney with a fresh air dried linen-like undertone".

EXAMPLE VI

PREPARATION OF COSMETIC POWDER COMPOSITIONS

Cosmetic powder compositions are prepared by mixing in a ball mill, 100 grams of talcum powder (per compositions) with 0.25 grams of the substance set forth in Table II below (per composition). Each of the cosmetic powder compositions has an excellent aroma as described in Table II below:

TABLE II

| Substance | Aroma Description |
|---|---|
| Mixture of compounds having the structures: 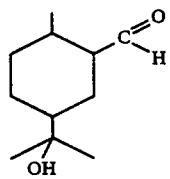 and 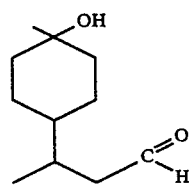 produced according to Example I, bulked distillation Fractions 4–6. | A woody, nutty aroma with minty and floral topnotes. |
| Mixture of compounds having the structures: 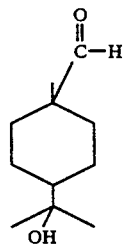 and 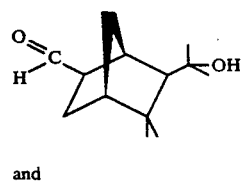 produced according to Example II, bulked distillation Fractions 5–8 | A floral (lilac) aroma with floral (lilac-like) and cinnamon-like topnotes. |
| Compound having the structure: | A green, woody, peach-like and balsamic aroma with green and floral topnotes. |
| produced according to Example III, bulked distillation Fractions 5–8 Mixture of compounds having the structures: and produced according to Example IV, bulked distillation Fractions 4–8 | A fresh air dried linen aroma. |
| Perfume composition of Example V-A | Piney, having woody and nutty undertones and minty and floral topnotes. |
| Perfume composition of Example V-B | Piney, having lilac undertones and floral (lilac-like) and cinnamon-like topnotes. |
| Perfume compositions of Example V-C | Piney, with green, woody, peach-like and balsamic undertones and green, floral topnotes. |
| Perfume compositions of Example V-D | Piney, with a fresh air dried linen-like undertone. |

EXAMPLE VII

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table II of Example VI, are prepared containing 0.10%, 0.15%, 0.20%, 0.25%, 0.30% and 0.35% of the substance set forth in Table II of Example VI. They are prepared by adding and homogeneously mixing the appropriate quantity of substance set forth in Table II of Example VI in the liquid detergent. The detergents all possess excellent aromas as set forth in Table II of Example VI, the intensity increasing with greater concentrations of substance as set forth in Table II of Example VI.

EXAMPLE VIII

PREPARATION OF COLOGNES AND HANDKERCHIEF PERFUMES

Compositions as set forth in Table II of Example VI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VI are imparted to the colognes and to the handkerchief perfumes at all levels indicated.

EXAMPLE IX

PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table II of Example VI until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VI.

EXAMPLE X

PREPARATION OF SOLID DETERGENT COMPOSITIONS

Detergents are prepared using the following ingredients according to Example I of Canadian Pat. No. 1,007,948 (incorporated herein by reference):

| Ingredient | Percent by Weight |
|---|---|
| Neodol ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table II of Example VI. Each of the detergent samples has an excellent aroma as indicated in Table II of Example VI.

EXAMPLE XI

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

| | |
|---|---|
| 1. | A water "dissolvable" paper ("Dissolvo Paper") |
| 2. | Adogen 448 (m.p. about 140° F.) as the substrate Coating; and |
| 3. | An outer coating having the following formulation (m.p. about 150° F.): 57% $C_{20-22}$HAPS 22% isopropyl alcohol 20% antistatic agent 1% of one of the substances as set forth in Table II of Example VI. |

Fabric softening compositions prepared according to Example I at column 15 of U.S. Pat. No. 3,632,396 having aroma characteristics as set forth in Table II of Example VI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example VI, supra.

EXAMPLE XII

HAIR SPRAY FORMULATION

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table II of Example VI, supra | 0.10 weight percent |

The perfuming substances as set forth in Table II of Example VI add aroma characteristics as set forth in Table II of Example VI which are rather intense and aesthetically pleasing to the users of the soft-feel, good-hold pump hair sprays.

EXAMPLE XIII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A and COMPOSITION B are then mixed in a 50:50 wt ratio of A:B and cooled to 45° C. and 0.3 wt percent of perfuming substance as set forth in Table II of Example VI is added to the mixture. The resulting mixture is cooled to 40° C. and blending is carried out for an additional one hour in each case. At the end of this blending period, the resulting material has a pleasant fragrance as indicated in Table II of Example VI.

PATENTS INCORPORATED HEREIN BY REFERENCE

The following patents referred to supra, are hereby incorporated herein by reference:
U.S. Pat. No. 3,632,396
U.S. Pat. No. 3,948,818
Canadian Pat. No. 1,007,948.
What is claimed is:
1. A compound having the structure:

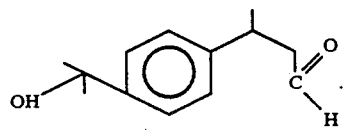

2. A perfume process for augmenting or enhancing the aroma of a consumable materiala selected from the group consisting of perfume compositions and perfumed polymers, comprising the step of intametly admixing with said consumable material, an aroma augmenting or enhancing quantity of a compound defined in claim 1.

* * * * *